United States Patent [19]

Maender et al.

[11] 4,209,463

[45] Jun. 24, 1980

[54] PROMOTING THE FORMATION OF NITRODIARYLAMINES FROM NITROHALOARENES, ACTIVATED ARYL AMINES AND SODIUM CARBONATES

[75] Inventors: Otto W. Maender, Copley; Robert L. Wright, Fairlawn, both of Ohio

[73] Assignee: Monsanto Company, St. Louis, Mo.

[21] Appl. No.: 864,196

[22] Filed: Dec. 27, 1977

[51] Int. Cl.$^2$ ............................................. C07C 85/04
[52] U.S. Cl. .................................... 260/576; 260/571
[58] Field of Search ................................ 260/576, 571

[56] References Cited

U.S. PATENT DOCUMENTS

| | | | |
|---|---|---|---|
| 2,479,205 | 8/1949 | Buckley et al. | 260/570 |
| 2,887,514 | 5/1959 | Schmerling | 260/577 |
| 2,924,620 | 2/1960 | Miller | 260/576 |
| 2,927,943 | 3/1960 | Merz | 260/576 |
| 3,065,269 | 11/1962 | Dent | 260/576 |
| 3,121,736 | 2/1964 | Luvisi et al. | 260/576 |
| 3,393,241 | 7/1968 | Nielsen | 260/576 |

FOREIGN PATENT DOCUMENTS

| | | | |
|---|---|---|---|
| 498077 | 12/1953 | Canada | 260/576 |
| 614158 | 2/1961 | Canada | 260/576 |
| 1056619 | 5/1959 | Fed. Rep. of Germany | 260/576 |
| 1090225 | 10/1960 | Fed. Rep. of Germany | 260/576 |
| 855719 | 12/1960 | United Kingdom | 260/576 |
| 1434320 | 5/1976 | United Kingdom | 260/576 |
| 1455207 | 11/1976 | United Kingdom | 260/576 |

OTHER PUBLICATIONS

Scardiglia et al., "J. Org. Chem., " vol. 23, pp. 629–631 (1958).
Rondestvedt, "J. Org. Chem.", 42(10), pp. 1786–1790 (1977).
Sharnin et al., "J. Org. Chem. USSR", 6, pp. 990–992 (1970).
Bhattacharyya et al., "Chem. Ab.", 68 (21623z) (1968).

*Primary Examiner*—John Doll
*Attorney, Agent, or Firm*—Gordon B. Seward

[57] ABSTRACT

Forming nitrodiarylamines by reacting the formyl derivative of an aromatic amine, a nitrohaloarene, and a proton abstractor which is sodium carbonate or bicarbonate with or without a reaction promoting amount of a compound of potassium, cesium, rubidium or mixture thereof.

8 Claims, No Drawings

PROMOTING THE FORMATION OF NITRODIARYLAMINES FROM NITROHALOARENES, ACTIVATED ARYL AMINES AND SODIUM CARBONATES

The invention relates to the preparation of nitrodiarylamines which are valuable intermediates for the preparation of dyestuffs and antidegradants. For example, 4-nitrodiphenylamine is an important intermediate for rubber antidegradants. The invention particularly relates to the preparation of 4-nitrodiphenylamine from p-nitrochlorobenzene.

The Ullmann condensation has been used in several modifications to form diarylamines, all involving reaction of an aryl halide with an aryl amine, one or both of which contains an activating substituent and usually with a copper catalyst. By utilization of the formyl derivative as an activated form of the aryl amine, and a nitrohalobenzene as an activated form of the axyl halide, the reaction can be effected without the usual copper catalyst, providing there is present a so-called acid acceptor for which purpose potassium carbonate is commonly used. There is an economic incentive to use sodium salts but sodium carbonate is significantly less effective.

In accordance with the present invention, a process of making nitrodiarylamines has been discovered which comprises reacting the formyl derivative of an aromatic amine with nitrohaloarene containing reactive halogen in the presence of a sodium salt containing the carbonate anion, i.e. either sodium carbonate, bicarbonate or mixture thereof and a reaction-promoting amount of a compound of potassium, cesium or rubidium. The anion of the promoter appears to be largely a matter of choice, examples being halide, particularly chloride, bromide, fluoride or iodide, silicate, particularly meta-silicate $SiO_3$—, phosphate, particularly ortho-phosphate, $PO_4$—, mono H ortho-phosphate or di H ortho-phosphate carbonate, bicarbonate, sulfate, acyl such as formate, acetate or benzoate, hydroxide or the anion from an amide, particulary the formyl derivative of an aromatic primary amine. The potassium, cesium or rubidium compound is believed to promote the removal of a proton from the formyl derivative of the aromatic amine. Thus, the sodium carbonate is believed to be a proton abstractor rather than an acid acceptor.

The potassium, cesium and rubidium salts of N-formylaromatic amines may be prepared from the corresponding alkali metal alkoxides in dimethyl formamide or xylene, the alcohol being constantly removed to drive the reaction to completion. Potassium formanilide is a crystalline white solid m.p. 184°–186° C. If the only proton abstractor is sodium carbonate or bicarbonate, it should be used at least in molar equivalent amount based on the sodium content to the nitrohaloarene to be converted. However, optimum results require more than the theoretical equivalent of proton abstractor and it is preferred to use about 1.4 molecular equivalents per mole of nitrohaloarene. If a carbonate is used as the promoter, the sodium carbonate or bicarbonate may, for example, be in the range of 0.5–2.0 molar equivalents per mole of nitrohaloarene in combination with such amounts of carbonate promoter as to total, preferably, about 1.4 molar equivalents per mole of nitrohaloarene. As noted, the total carbonate charge should be at least the molar equivalent of the nitrohaloarene and usually it will be within the range of 1.4–2.7 molar equivalents per mole of nitrohaloarene. It should be understood that in the practice of the invention, at least half and preferably the major portion of the proton abstractor on an acid equivalent basis is a sodium salt or mixture of sodium salts.

The amount of promoter will depend upon the results desired. In general, the promoter expressed as molar equivalent of potassium, cesium or rubidium per mole of nitrohaloarene will fall within the range of 0.02–1.2 molar equivalent per mole of nitrohaloarene. For example, potassium chloride, an effective and economical promoter is active down to at least about 0.02 moles per mole of p-nitrochlorobenzene. The promoting effect of potassium chloride is surprising in view of the fact that it is a by-product in the reaction with potassium carbonate acceptor. The yields, within limits, are relatively insensitive to the amount of promoter. The effect of increasing amounts of promoter is decreasing reaction times. However, it is believed that amounts of promoter exceeding the solubility in the reaction medium have little or no benefit.

The physical properties of the sodium carbonate or bicarbonate significantly influence the results. Small particle size is advantageous. For example, commercial grade soda ash of low bulk density and fine particle size is preferred to dense, coarse material. Results are improved with the latter, however, after grinding to 50 mesh or finer. Similarly, in the case of potassium chloride promoter results are improved by using material of 50 mesh size or finer.

Illustrative of suitable nitrohaloarenes are: o-nitrochlorobenzene, o-nitrobromobenzene, p-nitrochlorobenzene, p-nitrobromobenzene, m-nitrochlorobenzene, m-nitrobromobenzene, 1-chloro-2-methyl-4-nitrobenzene, 1-chloro-3-methyl-4-nitrobenzene, 1-chloro-2-nitronaphthalene, 3,4-dichloronitrobenzene, 3-methyl-4-chloronitrobenzene, 2-methyl-4-chloro-nitrobenzene, 2-ethyl-4-chloro-nitrobenzene, 2,3-dimethyl-4-chloronitrobenzene, 2,5-dimethyl-4-chloronitrobenzene and 3,5-dimethyl-4-chloronitrobenzene.

The formyl derivative is preferably formanilide or formanilide substituted in the benzene nucleus by one or more inactive substituents such as alkyl, alkoxy, fluoro or chloro substituents. Illustrative examples of formanilides useful as intermediates for the process are: formanilide, m-chloroformanilide, p-chloroformanilide, 2-methylformanilide, 3-methylformanilide, 4-methylformanilide, 3-ethylformanilide, 3,4-dimethylformanilide, 3-methoxyformanilide, 4-methoxyformanilide, 4-ethylformanilide, 4-isopropylformanilide, 4-butylformanilide, 3,4-dichloroformanilide and 4-nitroformanilide.

If desired, an inert solvent such as xylene, cumene or diisopropylbenzene may be used in carrying out the reaction. The formamide reactant itself serves as a solvent and is preferably used in excess of the molar quantity to be reacted. Other suitable solvents are dimethyl formamide and dimethylsulfoxide. A solvent may serve to control the reaction temperature which will usually be 180°–235° C. and preferably 210°–230° C. An inert solvent such as xylene may also aid in the removal of by-product water, the removal of which is important for maximum yields and efficiencies. The temporary presence of small amounts of water is not detrimental. As hereinafter shown, hydrated salts may be used as promoters.

The reaction may be carried out in mild steel, stainless steel, glass or glass-lined vessels. After the condensation reaches the selected end-point, the salt by-product may be removed by water washing; solvent, if present, removed by distillation, and the residue cooled to about 5° C. to recover 4-nitrodiphenylamine by recrystallization.

EXAMPLE 1

Into a suitable reactor fitted with a water trap, stirrer, condenser and thermometer is charged 60.7 parts by weight (0.385 mole) of p-nitrochlorobenzene, 93.3 parts by weight (0.77mole) of formanilide in xylene, and 70.6% solution, 28.6 parts by weight (0.27 mole) of sodium carbonate and 22.4 parts by weight (0.30 mole) of potassium chloride. The mixture is gradually heated and stirred at about 215° C. for 2.5 hours, during which time by-product water is collected. The xylene solution is then washed with water, separated from the water and cooled. The crystals of 4-nitrodiphenylamine which form are separated by filtration and washed with a little xylene. The yield is about 79% and conversion of the p-nitrochlorobenzene about 91%.

EXAMPLES 2-11

The effects of varying the amount of KCl and the temperature are illustrated in Table I. The runs are carried out as described in Example 1 with 0.385 mole of p-nitrochlorobenzene, 0.77 mole of formanilide in xylene and 0.27 mole of sodium carbonate except as noted. Examples 3 and 4 are replicates of Example 1. Examples 9 and 10 are comparative examples outside the invention of which Example 9 is a control without promoter and Example 10 replaces KCl of Example 8 with NaCl. The advantage of KCl is evident.

TABLE I

| Example No. | KCl moles | Temperature °C. | Time Hrs. | Yield % | Conversion of p-nitro chlorobenzene % |
|---|---|---|---|---|---|
| 2 | .15 | 210 | 3 | 75.8 | 88.1 |
| 3 | .30 | 215 | 3.25 | 77.8 | 88.8 |
| 4 | .30 | 215 | 2.0 | 76.3 | 86.5 |
| 5 | .45 | 215 | 2.5 | 78.4 | 89.8 |
| 6 | .30 | 225 | 1.25 | 80.4 | 91.4 |
| 7 | .30 | 235 | .75 | 80.5 | 93.5 |
| 8 | .30 | 230 | 1.25 | 85.1 | 97.1 |
| 9 | none | 230 | 1.75 | 67.0 | 84.3 |
| 10 | .3NaCl | 230 | 1.75 | 69.3 | 84.0 |
| 11* | .3 | 230 | .75 | 80.8 | 92.9 |

*used .385 mole of sodium carbonate.

EXAMPLES 12-18

The effect of KCl as a promoter is also exhibited at lower formanilide levels. Examples 12-18 illustrate promotion by KCl in runs with 0.54 moles of formanilide in xylene, 0.385 moles of p-nitrochlorobenzene and 0.27 moles of sodium carbonate at 225°-230° C. Example 12, outside the invention, is a control without promoter. The moles of KCl in the aforesaid charge, time of heating (reaction time) yield and conversion of p-nitrochlorobenzene (PNCB) are summarized in Table II. It will be noted that there is little advantage from using more than 0.1 mole of KCl (about 0.26 mole per mole of p-nitrochlorobenzene).

TABLE II

| Example No. | KCl moles | Reaction time hours | Yield % | Conversion of PNCB % |
|---|---|---|---|---|
| 12 | none | 5 | 64.6 | 80.8 |
| 13 | .03 | 5[1] | 73.0 | 80.1 |
| 14 | .10 | 1.7[2] | 70.8[2]ave. | 86.8[2]ave. |
| 15 | .20[3] | 5.0[4] | 74.3 | 84.9 |
| 16 | .20 | 1.3 | 71.1 | 85.9 |
| 17 | .30 | 1.7[5] | 71.9[5]ave. | 88.1ave. |
| 18 | .30 | 1.0[6] | 76.1 | 84.0 |

[1]reaction temperature 203°-209° C.
[2]figure is average of six replicates.
[3]used with 0.20 moles of $Na_2CO_3$.
[4]reaction temperature 204°-209° C.
[5]figure is average of three replicates.
[6]reaction temperature 233° C.

EXAMPLES 19-34

Examples 19-34 illustrate the use of potassium carbonate as the promoter in reactions of 0.385 moles of p-nitrochlorobenzene, 0.54 moles of formanilide in xylene and the indicated moles of sodium and potassium carbonate. Examples 19 and 20 are control experiments outside the invention with only $K_2CO_3$ $Na_2CO_3$, respectively.

TABLE III

| Ex. No. | $Na_2CO_3$ Moles | $K_2CO_3$ Moles | Time Minutes | Temperature °C. | Yield % | Conversion of PNCB % |
|---|---|---|---|---|---|---|
| 19 | none | .27 | 44[1] | 205-210 | 79.2[1] | 91.2[1] |
| 20 | .27 | none | 300 | 203-207 | 61.6 | 64.8 |
| 21 | .24 | .03 | 300 | 205-210 | 79.5 | 90.7 |
| 22 | .24 | .03 | 330 | 205-210 | 76.1 | 86.3[2] |
| 23 | .20 | .10 | 185 | 210 | 76.0 | 88.2 |
| 24 | .16 | .11 | 270 | 210 | 72.4 | 83.3 |
| 25 | .20 | .12 | 193[3]ave. | 210 | 72.2[3]ave. | 88.2[3]ave. |
| 26 | .20[4] | .12[4] | 123[5]ave. | 210 | 74.2[5]ave. | 86.3[5]ave. |
| 27 | .30 | .12 | 174 | 210 | 73.8 | 89.3 |
| 28 | .40 | .12 | 162 | 210 | 71.5 | 91.6 |
| 29 | .14 | .13 | 235 | 210 | 75.5 | 88.9 |
| 30 | .20 | .16 | 153 | 210 | 72.5 | 89.3 |
| 31 | .20 | .18 | 138 | 210 | 72.2 | 89.2 |
| 32 | .10 | .20 | 141 | 211 | 70.6 | 87.8 |
| 33 | .20 | .12 | 94 | 220 | 73.2 | 89.0 |
| 34 | .15 | .15 | 45 | 230-235 | 77.9 | 90.5 |

[1]the figure is the average of five runs.
[2]a third run with .24 $Na_2CO_3$ discontinued after 5 hours at which time the gas evolution was still low is not included. Example 22 was run with a distillation head instead of a water separator.
[3]the figure is the average of three runs.
[4]ground to 50 mesh size.
[5]the figure is the average of four runs.

The results in Table III show that sodium carbonate is inferior to potassium carbonate. However, replacement of as little as 0.03 moles of sodium carbonate with potassium carbonate increases the yield more than 15% and gives yields and conversions approaching those with potassium carbonate. In general, the effect of increasing the amount of potassium carbonate used with sodium carbonate is to increase the reaction rate. The combination of 0.20 mole of sodium carbonate and 0.10-0.12 mole of potassium carbonate (about 0.52-0.62 mole equivalent per mole of p-nitrochlorobenzene) gives reaction rate, yields and conversions feasible for commercial production and at the same time achieves a substantial reduction in potassium carbonate usage. Neither higher nor lower amounts of sodium carbonate appear advantageous. If desired, the potassium carbonate may be supplemented with another promoter such as potassium chloride. However, the addition of potassium chloride gives minimal advantage at least where 0.1 mole of potassium carbonate is charged.

Grinding the carbonates to 50 mesh size decreases reaction time and increases yield but the improvement requires grinding both components.

EXAMPLES 35-39

The following examples illustrate the use of various promoters in reactions of 0.385 mole of p-nitrochlorobenzene, 0.54 mole of formanilide in xylene and 0.27 mole sodium carbonate and 0.03 mole of promoter. The reactions are carried out in xylene as described in Example 1 for the indicated times and temperatures. For convenience of comparison with the control the results without promoter, Example 20, supra, are repeated in Table IV. Example 39 is a comparative example outside the invention. Also, the promoter alone is insufficient. For example, omitting the sodium carbonate from Example 36 gives only a 30.6% yield. Higher yields and conversions are obtained in less time by practice of the present invention.

TABLE IV

| Example No. | Promoter | Heating time, hrs. and temp. °C. | Yield % | Conversion of p-nitrochloro benzene % |
|---|---|---|---|---|
| control | none | 5/203-207 | 61.6 | 64.8 |
| 35 | cesium acetate x H₂O | 3/194-205 | 83.8 | 95.9 |
| 36 | potassium acetate | 4/203-210 | 77.2 | 89.0 |
| 37 | rubidium acetate | 3/202-209 | 79.4 | 91.5 |
| 38 | potassium fluoride | 3/205-208 | 73.6 | 85.1 |
| 39 | barium acetate | 5/202-209 | 65.7 | 75.0 |

EXAMPLES 40-44

Examples 40-44 illustrate the effect of 0.01 mole of promoter in reaction of 0.385 moles of p-nitrochlorobenzene, 0.54 mole of formanilide as a 71% solution in xylene and 0.27 mole of sodium carbonate. The reactants are heated at 205°-10° C. with 0.01 mole of promoter for the indicated times. Example 40 is a control without promoter. In examples 43 and 44, the total liters of gas evolved are shown in parentheses. The evolution of 12 liters in three hours in Example 44 shows that the rate of formation of 4-nitrodiphenylamine is faster than in control Example 43. It will also be noted that the promoter increases the yield of 4-nitrodiphenylamine more than 10%.

TABLE V

| Example | Promoter | Heating Time, Hours | Yield, % | Conversion of p-nitrochloro-benzene % |
|---|---|---|---|---|
| 40 | Cs Cl | 2 | 76.9 | 91.9 |
| 41 | Cs acetate | 1.75 | 72.4 | 87.5 |
| 42 | Cs carbonate | 2 | 72.9 | 88.2 |
| 43 | none | 5(12.1 l.) | 60.8 | 72.0 |
| 44 | KCl | 5[1](14 l.) | 71.6 | 85.1 |

[1] required 3 hours to reach 12 l. of CO

EXAMPLES 45-47

As illustrative of promoting the reaction using sodium bicarbonate as the proton abstractor 0.385 mole of p-nitrochlorobenzene, 0.54 mole of formanilide as a 65.8% solution in xylene and 0.54 mole of sodium bicarbonate are heated at 220° C. with promoter for the times indicated below. Example 45 is a control without promoter.

TABLE VI

| Example | Promoter | Moles | Heating time, mins. | Yield, % | Conversion, % |
|---|---|---|---|---|---|
| 45 | none | — | 160 | 63.8 | 81.5 |
| 46 | KCl | 0.1 | 85 | 69.2 | 85.8 |
| 47 | Cs Cl | 0.03 | 23 | 71.2 | 87.2 |

It will be noted from the foregoing results that as compared to sodium bicarbonate alone, the reaction time is greatly reduced and yield improved with small amounts of promoter on a metal ion equivalent basis per mole of p-nitrochlorobenzene.

EXAMPLE 48

The promoting effect of potassium hydroxide is illustrated by charging to a suitable reactor fitted with a water trap, stirrer, condenser, metering device for addition of liquid, thermometer and gas collection system, 60.6 parts by weight (0.385 mole) of p-nitrochlorobenzene, 65.7 parts by weight (0.54 mole) of formanilide as a 65.8% solution in xylene and 28.4 parts by weight (0.27 mole) of sodium carbonate. The mixture is heated to refluxing temperature (reaction temperature) and stirred for about 2-5 hours during the first 37 minutes of which about 5.6 parts by weight 0.1 molecular proportions of KOH is added as a 45% aqueous solution. The water is continuously removed during the heating period and the reaction discontinued after collecting 14.8 liters of gas. The yield of 4-nitrodiphenylamine is 72%, and conversion of p-nitrochlorobenzene 94.9%. A similar experiment carried out without the potassium hydroxide to 14.8 liters of gas evolution (Experiment 12 above) gives a 64.6% yield and 80.8% conversion in 5 hours.

Although the invention has been illustrated by typical examples, it is not limited thereto. Changes and modifications of the examples of the invention herein chosen for purposes of disclosure can be made which do not constitute departure from the spirit and scope of the invention.

The embodiments of the invention in which an exclusive property or privilege is claimed are defined as follows:

1. A process which comprises forming nitrodiarylamine by reacting the formyl derivative of an aromatic amine, nitrohaloarene containing reactive halogen, proton abstractor, at least half the proton abstractor on an acid equivalent basis being a sodium salt containing the $CO_3$— anion or mixture thereof and a reaction promoting amount of a compound of potassium, cesium, rubidium or mixture thereof.

2. The process which comprises forming nitrodiarylamine by reacting (A) formanilide or formanilide substituted in the benzene nucleus by one or more alkyl, alkoxy, fluoro or chloro substituents with (B) nitrohalobenzene (C) proton abstractor, at least the major proportion of an acid equivalent basis being $Na_2CO_3$, $NaHCO_3$ or mixture thereof and (D) a reaction promoting amount of a potassium salt up to about 0.8 molar equivalent of potassium per mole of nitrohalobenzene.

3. The process of claim 2 wherein (A) is formanilide, (B) is p-nitrochlorobenzene, (C) is $Na_2CO_3$ and (D) is KCl.

4. The process of claim 2 wherein (A) is formanilide, (B) is p-nitrochlorobenzene, (C) is $Na_2CO_3$ and (D) is $K_2CO_3$.

5. The process of claim 1 wherein the formyl derivative of the aromatic amine is formanilide, the nitrohaloarene is p-nitrochlorobenzene, the proton abstractor is $Na_2CO_3$ and the compound of potassium, cesium, rubidium or mixture thereof is a cesium compound.

6. The process which comprises forming 4-nitrodiphenylamine by reacting formanilide, p-nitrochlorobenzene, $Na_2CO_3$ in amount at least the molar equivalent based on the sodium content to the p-nitrochlorobenzene and at minor proportions a reaction promoting amount of a compound of potassium, cesium, rubidium or mixture thereof.

7. The process of claim 6 in which the promoter is KCl in amount up to about 0.26 mole per mole of p-nitrochlorobenzene.

8. The process of claim 6 in which the promoter is potassium carbonate in amount up to about 0.62 molar equivalent per mole of p-nitrochlorobenzene.

* * * * *